(12) United States Patent
Hayashi et al.

(10) Patent No.: US 8,900,606 B2
(45) Date of Patent: Dec. 2, 2014

(54) METHODS OF APPLYING COATING MATERIALS FOR SOLID MEDICINES

(71) Applicant: Toray Industries, Inc., Tokyo (JP)

(72) Inventors: Yuki Hayashi, Kamakura (JP); Yuki Fujisaki, Kamakura (JP); Ryoji Yoshii, Kamakura (JP)

(73) Assignee: Toray Industries, Inc. (JP)

( * ) Notice: Subject to any disclaimer, the term of this patent is extended or adjusted under 35 U.S.C. 154(b) by 83 days.

(21) Appl. No.: 13/796,006

(22) Filed: Mar. 12, 2013

(65) Prior Publication Data

US 2013/0189325 A1 Jul. 25, 2013

Related U.S. Application Data

(62) Division of application No. 13/141,168, filed as application No. PCT/JP2009/071573 on Dec. 25, 2009.

(30) Foreign Application Priority Data

Dec. 25, 2008 (JP) ................ 2008-329678

(51) Int. Cl.
*A61K 9/30* (2006.01)
*A61K 9/42* (2006.01)
*A61K 47/02* (2006.01)
*A61K 9/28* (2006.01)
*A61K 47/32* (2006.01)

(52) U.S. Cl.
CPC ........... *A61K 47/02* (2013.01); *A61K 9/2813* (2013.01); *A61K 9/2826* (2013.01); *A61K 9/284* (2013.01); *A61K 47/32* (2013.01)
USPC ........................ 424/400; 424/475; 424/476

(58) Field of Classification Search
USPC ....................................... 424/400
See application file for complete search history.

(56) References Cited

U.S. PATENT DOCUMENTS

| 4,645,794 A | 2/1987 | Davis et al. |
| 5,981,029 A | 11/1999 | Harada et al. |
| 2006/0034905 A1 * | 2/2006 | Singh et al. ............. 424/449 |
| 2006/0134215 A1 | 6/2006 | Kondo et al. |
| 2006/0229383 A1 | 10/2006 | Noami et al. |
| 2009/0291138 A1 | 11/2009 | Watanabe et al. |
| 2009/0312462 A1 * | 12/2009 | Oakley et al. ............. 524/47 |
| 2010/0272831 A1 | 10/2010 | Lagaron Cabello et al. |
| 2011/0132975 A1 * | 6/2011 | Toft et al. ............. 229/5.84 |
| 2012/0321677 A1 | 12/2012 | Fujisaki et al. |

FOREIGN PATENT DOCUMENTS

| EP | 2412369 A1 | 2/2012 |
| JP | 51-57814 A | 5/1976 |
| JP | 51-57815 A | 5/1976 |
| JP | 51-70808 A | 6/1976 |
| JP | 52-58766 | 5/1977 |
| JP | S59-15457 A | 1/1984 |
| JP | 9-150484 A | 6/1997 |
| JP | H09-315903 A | 12/1997 |
| JP | 11-315222 A | 11/1999 |
| JP | 2006-188490 A | 7/2006 |
| JP | 2008-201712 A | 9/2008 |
| JP | 2009-007295 A | 1/2009 |
| RU | 1812992 A3 | 4/1993 |
| WO | WO 0049072 A1 * | 8/2000 |
| WO | 2005/019286 A1 | 3/2005 |
| WO | 2008/069262 A1 | 12/2008 |

OTHER PUBLICATIONS

Okajima, T. et al., "Piezoelectric Admittance Measurements of Montmorillonite/Poly(vinyl alcohol) Composite Film-Coated Quartz Crystal Oscillators," *Bull. Chem. Soc.*, vol. 65, 1992, pp. 1884-1890.

Rocha, H.V.A et al., "The Preparation and Evaluation of Sodium and Alkylamonium Montmorillonite and Polysaccharide Nanocomposites as Sustained Release Excipients," *Polymer-Plastics Technology and Engineering*, vol. 47, Issue 12, 2008, pp. 1256-1264.

* cited by examiner

*Primary Examiner* — Michael G Hartley
*Assistant Examiner* — Robert Cabral
(74) *Attorney, Agent, or Firm* — DLA Piper LLP (US)

(57) ABSTRACT

A method improves stability of drugs in a solid pharmaceutical formulation against oxygen and water vapor by coating the solid pharmaceutical formulation with a coating material including a high hydrogen-bonding resin and a swelling clay.

8 Claims, 4 Drawing Sheets

Fig. 3
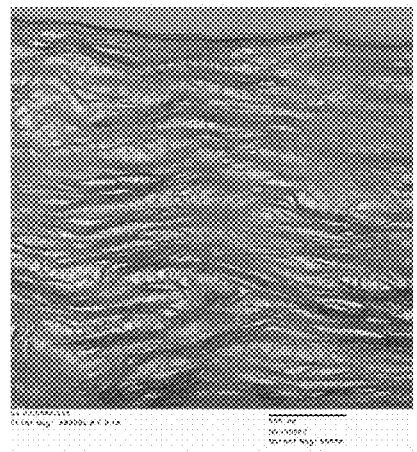
[Fig. 4]
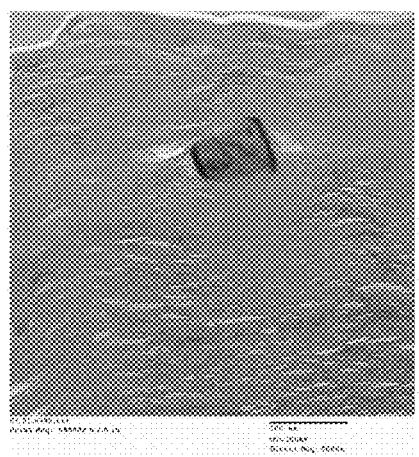

METHODS OF APPLYING COATING MATERIALS FOR SOLID MEDICINES

RELATED APPLICATIONS

This is a divisional of U.S. application Ser. No. 13/141,168 filed Jun. 21, 2011, which is a §371 of International Application No. PCT/JP2009/071573, with an international filing date of Dec. 25, 2009 (WO 2010/074223 A1, published Jul. 1, 2010), which is based on Japanese Patent Application No. 2008-329678, filed Dec. 25, 2008, the subject matter of which is incorporated by reference.

TECHNICAL FIELD

This disclosure relates to a coating material (coating agent) for a solid formulation and methods of applying coating materials for solid medicines.

BACKGROUND

It is known that many pharmaceuticals are not stable against oxygen and water vapor and that some change occurs in about 40% of pharmaceuticals when they are left to stand in unpacked condition, thereby causing a fatal problem in the pharmaceutical quality. Therefore, most of the commercially available pharmaceuticals, especially solid formulations, are packaged with a packaging material such as PTP (press through pack) sheet and protected from oxygen and water vapor. In recent years, PTP sheets in which polyvinylidene chloride having superior water vapor barrier property (moisture resistance) and oxygen barrier property are laminated have been developed and put into practice.

As a method of improving the stability of a solid formulation against oxygen and water vapor, methods of sugar-coating the solid formulation and methods of film-coating the solid formulation with a macromolecular substance have been put into practice. In the latter film-coating methods, polyvinyl alcohols and sodium carboxymethyl cellulose are known as a macromolecular substance exhibiting oxygen barrier property, and as a macromolecular substance exhibiting water vapor barrier property, aminoalkyl methacrylate copolymer E (Eudragit EPO (registered trademark); Degusssa Co.) is known.

Recently, as a macromolecular substance having an improved oxygen barrier property, a resin composition obtained by copolymerizing a polyvinyl alcohol and a polymerizable vinyl monomer (WO 05/019286) and a coating material obtained by adding talc and a surfactant to a polyvinyl alcohol (JP 2006-188490 A) have been developed to try to improve the stability of solid formulations. In addition, in the field of packaging films, as a method of improving gas barrier properties (oxygen barrier property and water vapor barrier property) in high humidity, methods of dispersing an intercalation compound in a polyvinyl alcohol have been proposed (JP 11-315222 A and JP 9-150484 A).

Meanwhile, at medical sites and dispensing pharmacies, to prevent patients from forgetting to take their prescribed drugs or making mistakes in the dosage thereof, it is widely practiced to use single-dose formulation which is prepared by taking a plurality of pharmaceuticals to be taken at once out of the respective packaging material such as PTP sheet and provides them altogether in one bag.

However, in those pharmaceuticals used in single-dose formulations, although the stability against oxygen and water vapor is ensured by the packaging material such as PTP sheet at the stage when the pharmaceuticals are put onto the market, since they are stored in unpacked condition over a prolonged period at medical scenes and the like, there is a risk of causing a deterioration in the quality of the pharmaceuticals.

To avoid this risk, there is a method of sugar-coating a solid formulation. However, sugar-coating of a solid formulation not only requires a long processing time, but also makes the resulting solid formulation excessively large, rendering it difficult for patients to take. Consequently, there are currently limited cases where this method is applicable. In addition, at present, the existing methods of film-coating a solid formulation cannot allow the resulting solid formulation to exhibit sufficient oxygen barrier property in high humidity, and even when the resin composition according to WO '286 is used, the resulting oxygen barrier property falls short of that of a packaging material such as PTP sheet. In the field of packaging films, there are coating materials having superior oxygen barrier property. However, they cannot be applied to a solid formulation since they are laminated films with a substrate film.

In view of the above, it could be helpful to provide a coating material for a solid formulation which is capable of stably retaining the quality of the effective ingredient in the solid formulation for a prolonged period even in unpacked condition in such a manner that the solid formulation can be used in a single-dose formulation.

SUMMARY

We intensively studied the possibility that a coating material in which a swelling clay forms specific laminated structures in high hydrogen-bonding resin imparts gas barrier properties equivalent or superior to those of a PTP sheet (oxygen permeability coefficient: less than $1 \times 10^{-4}$ $cm^3 \cdot mm/cm^2 \cdot 24$ hr·atm; water vapor permeability: less than $1 \times 10^{-4}$ $g \cdot mm/cm^2 \cdot 24$ hr·atm) to a solid formulation.

We thus provide a coating material for a solid formulation which comprises a high hydrogen-bonding resin and a swelling clay. When this coating material is applied (coated) on a solid formulation and dried, a coating film in which the laminated structures of the aforementioned swelling clay are oriented planarly and dispersed in a network fashion is formed, so that the gas barrier properties of the coating material can be improved to a level equivalent or superior to those of a PTP packaging material. In addition, since the formed coating film is thinner than a sugar coat, the taking of the formulation by patients is not adversely affected as well.

In the aforementioned coating material, it is preferred that the ratio of the area occupied by the aforementioned planarly-oriented laminated structures be not less than 30% with respect to the area of the longitudinal section of the aforementioned coating film, and it is more preferred that the mass ratio of the high hydrogen-bonding resin and the swelling clay be 4:6 to 6:4. In this case, since the laminated structures of the swelling clay become likely to intertwine with each other, the gas barrier properties of the resulting coating film can be further improved.

Further, it is preferred that the aforementioned coating material comprise a sugar alcohol derivative-type surfactant. In this case, it is preferred that the mass ratio of the aforementioned high hydrogen-bonding resin and the aforementioned swelling clay be 2:8 to 5:5 and that the content of the aforementioned sugar alcohol derivative-type surfactant be 7 to 35%. When the aforementioned coating material comprises a sugar alcohol derivative-type surfactant, since the oxygen permeability coefficient and water vapor permeability of the formed coating film can be further decreased, the stability of the effective ingredient in the solid formulation against oxygen and water vapor can be further improved.

It is preferred that the aforementioned high hydrogen-bonding resin be a polyvinyl alcohol and that the aforementioned swelling clay be a bentonite. The polyvinyl alcohol improves the oxygen barrier property in low humidity and the bentonite is oriented planarly in parallel to the surface direction of the high hydrogen-bonding resin layer to produce path effect, so that the gas barrier properties in high humidity can be improved.

It is preferred that the aforementioned sugar alcohol derivative-type surfactant be a sorbitan fatty acid ester. When the aforementioned coating material comprises a sorbitan fatty acid ester, since the dispersion of the swelling clay is improved, the gas barrier properties can be improved.

Further, we provide a solid formulation coated with the aforementioned coating material. This solid formulation can retain the stability of the effective ingredient therein for a prolonged period even in unpacked condition in such a manner that the solid formulation can be used in a single-dose formulation.

A solid formulation can thus be coated with a thin coating film in such a manner that the taking thereof is not adversely affected, and gas barrier properties equivalent or superior to those of a packaging material such as PTP sheet can be imparted. Therefore, the solid formulation coated with the aforementioned coating material can retain the stability of the effective ingredient in the solid formulation for a prolonged period even in unpacked condition, so that the solid formulation can be used in single-dose formulation without causing a deterioration in the quality of the pharmaceutical.

Further, since the coating material has excellent moisture resistance and excellent disintegration property at the same time, it may be applied in coating not only sustained release formulations, but also immediate release formulations. In addition, since the coating material can be produced using a coating machine commonly used by those skilled in the art such as a continuous aeration coating machine, fluidized bed coating machine or pan coater, the coating material may be widely used and the coating operation thereof on a solid formulation can be easily carried out.

We provide a method of improving stability of drugs in a solid pharmaceutical formulation against oxygen and water vapor including coating the solid pharmaceutical formulation with a coating material including a high hydrogen-bonding resin and a swelling clay.

We also provide a method of improving gas barrier properties of a solid pharmaceutical formulation against oxygen and water vapor including coating the solid pharmaceutical formulation with a coating material including a high hydrogen-bonding resin and a swelling clay.

We further provide a method according of film-coating a solid pharmaceutical formulation comprising applying a coating material including a high hydrogen-bonding resin in a swelling clay to the solid pharmaceutical formulation.

Also, we provide a method of manufacturing a solid pharmaceutical formulation comprising coating the solid pharmaceutical formulation with a coating material including a high hydrogen-bonding resin and a swelling clay.

BRIEF DESCRIPTION OF THE DRAWINGS

FIG. 3 shows a focused ion beam-transmission electron micrograph of the coating film of Example 3.

FIG. 4 shows a focused ion beam-transmission electron micrograph of the coating film of Comparative Example 4.

DETAILED DESCRIPTION

Figure 1:
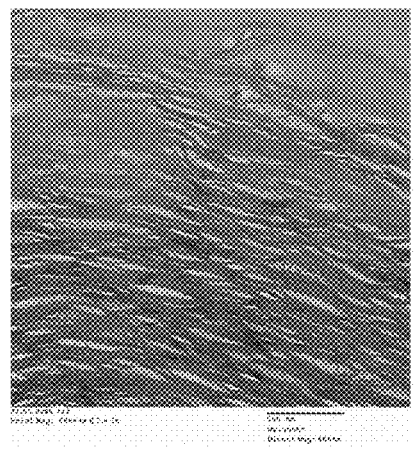
FIG. 1 shows a focused ion beam-transmission electron micrograph of the coating film of Example 1.

Preferred examples will now be described. However, this disclosure is not restricted to those examples and, unless otherwise specified, the unit "%" represents "mass-to-mass percentage (w/w %)."

The coating material is characterized by comprising a high hydrogen-bonding resin and a swelling clay. When the coating material is coated on a solid formulation and dried, since a coating film in which the laminated structures of the aforementioned swelling clay are oriented planarly and dispersed in a network fashion is formed, the gas barrier properties of the coating material can be improved to a level equivalent or superior to those of a PTP packaging material.

The term "coating material" refers to a composition which forms a thin coating film when coated on a solid formulation, thereby preventing the effective ingredient contained in the solid formulation from being degraded or the like by oxygen, water, light or the like. The aforementioned coating material can be prepared by dispersing it in an appropriate solvent in accordance with the intended use and utilized to coat a solid formulation and produce a coating film or film formulation. A coating film can be obtained by drying the solvent (water and the like) from the coating material or a solution containing the coating material, and a film formulation can be obtained by adding an effective ingredient to the coating material and subsequently drying in the same manner as in the case of the coating film production.

Examples of the aforementioned solvent include water, chain having 1 to not more than 5 carbon atoms (lower alcohols) and mixed solvents thereof, and water is particularly preferred.

The term "high hydrogen-bonding resin" refers to a resin having a high content of hydrogen-bonding group, and examples thereof include high hydrogen-bonding resins which satisfy a ratio of 5 to 60% in terms of the mass of the hydrogen-bonding group per unit resin mass. Examples of the hydrogen-bonding group include hydroxyl group, amino group, thiol group, carboxyl group, sulfonic acid group and phosphate group. As the high hydrogen-bonding resin used in the aforementioned coating material, a resin having a high content of hydroxyl group is more suitable. Examples of the aforementioned high hydrogen-bonding resin include polyvinyl alcohols and polysaccharides, and the high hydrogen-bonding resin is preferably a polyvinyl alcohol or sodium carboxymethyl cellulose, more preferably a polyvinyl alcohol. The polyvinyl alcohol may contain a derivative thereof. It is noted here that the aforementioned high hydrogen-bonding resin may be used in combination as long as the amount thereof is within the range which does not impair the gas barrier properties.

The aforementioned polyvinyl alcohol refers to one which is generally obtained by saponification of polyvinyl acetate and it encompasses partially saponified polyvinyl alcohols in which the acetate group remains in an amount of several 10%, as well as completely saponified polyvinyl alcohols in which the acetate group remains in an amount of only a few %. The saponification degree of the polyvinyl alcohol is preferably 70 to 97 mol %. The average polymerization degree is preferably 200 to 3,000, more preferably 600 to 2,400. As the aforementioned polyvinyl alcohol, two or more polyvinyl alcohols having different saponification degrees and average polymerization degrees may be used in combination. For mixing of two or more polyvinyl alcohols, for example, there is a method in which a polyvinyl alcohol having a low polymerization grade is added and then a polyvinyl alcohol having a high polymerization grade is mixed. Examples of the polyvinyl alcohol include various types of Poval (Kuraray Co., Ltd.) and Gohsenol (Nippon Synthetic Chemical Industry Co., Ltd.).

The term "swelling clay" refers to a clay having a swelling property. More particularly, the term refers to, among those fine powder substances that exhibit viscosity and plasticity when containing an appropriate amount of water, a substance having a swelling property.

As the swelling clay, one which is negatively charged due to the composition balance of the metal salt species is preferred, and examples thereof include smectites such as hydrated aluminum silicate having three-layer structure.

The term "negatively charged" refers to a condition in which the swelling clay has a cation exchange property, and the amount of the charge is expressed in the cation exchange capacity (CEC). The unit of cation exchange capacity is milligram equivalent/100 g (normally, expressed as "meq/100 g") and generally expressed in the number of equivalents corresponding to the molarity of monovalent ions.

Examples of the smectites include beidellite, nontronite, saponite, hectorite, sauconite, bentonite and aluminum magnesium silicate, and these may be used individually or two or more thereof may be used in combination as appropriate. Among such smectites, aluminum magnesium silicate and a bentonite are preferred, and a bentonite is more preferred. It is noted here that the aforementioned swelling clay may be used in combination as long as the amount thereof is within the range which does not impair the gas barrier properties.

The term "solid formulation" refers to a formulation in a solid form, and examples thereof include tablets (including sublingual tablets and orally-disintegrating tablets), capsules (including soft capsules and microcapsules), granules, subtle granules, powders, balls, troches and films.

Examples of the method of coating the solid formulation include, in cases where the solid formulation is in the form of a tablet, those coating methods using a coating pan or tablet coating machine; and in cases where the solid formulation is in the form of granules or powder, those methods using a fluidized bed coating machine or tumbling fluidized coating machine.

The term "laminated structure" refers to a structure in which a plurality of layered structures are laminated, and the term "orient planarly" means to arrange in parallel to the reference plane. That is, the term "a coating film in which the laminated structures of the swelling clay are oriented planarly and dispersed in a network fashion" refers to a coating film in which the bands of the swelling clay are laminated in 10 to 100 layers to form laminated structures which are arranged in almost parallel to the transverse section of the coating film (cross-section parallel to the coating film surface) and the bands are dispersed in a network fashion in the coating film. In this case, not only the bands are oriented completely in parallel, but also they may be oriented with undulations or in such a manner that the bands runs near or far from other bands running in all directions.

Since the aforementioned coating material for a solid formulation can form a thin coating film which prevents permeation of oxygen and water vapor on the surface of the solid formulation, the coating material can impart gas barrier properties equivalent or superior to those of a packaging material such as PTP sheet (oxygen permeability coefficient: less than $1 \times 10^{-4}$ cm$^3$·mm/cm$^2$·24 hr·atm; water vapor permeability: less than $1 \times 10^{-4}$ g·mm/cm$^2$·24 hr·atm) to the solid formulation.

In the aforementioned coating material, the ratio of the area occupied by the aforementioned planarly-oriented laminated structures is, with respect to the area of the longitudinal section (cross-section perpendicular to the coating film surface) of the aforementioned coating film, preferably not less than 30%, more preferably not less than 35%, still more preferably not less than 42%.

Further, in the aforementioned coating material, it is preferred that the mass ratio of the high hydrogen-bonding resin and the swelling clay be 4:6 to 6:4. When the mass ratio of the high hydrogen-bonding resin and the swelling clay is not higher than 3:7, the coating material becomes highly viscous, so that spraying thereof may become difficult. In this case, spraying may become possible by lowering the concentration of the coating material. However, there may arise another problem such as prolonged production time. Further, when the mass ratio of the high hydrogen-bonding resin and the swelling clay is not less than 7:3, gas barrier properties equivalent or superior to those of a packaging material such as PTP sheet may not be attained.

The term "sugar alcohol derivative-type surfactant" refers to a surfactant having a sugar alcohol skeleton in the molecule. Examples of the type of the sugar alcohol include mannitol, xylitol, maltitol, trehalose, inositol and sorbitol. Examples of surfactant having a structure in which a hydrophobic group is bound to the sugar alcohol via an ester bond include sorbitan fatty acid esters, polyoxyalkylene sorbitan fatty acid esters, sucrose fatty acid esters, sorbit fatty acid esters, polyoxyalkylene sorbit fatty acid esters, polyglycerols, polyglycerol fatty acid esters, glycerol fatty acid esters and polyoxyalkylene glycerol fatty acid esters.

As the sugar alcohol derivative-type surfactant used in the aforementioned coating material, a sorbitan fatty acid ester and a sucrose fatty acid ester are preferred, and a sorbitan fatty acid ester is more preferred. Further, among sorbitan fatty acid esters, those having a high ratio of monoester are preferred, and those having a HLB (Hydrophilic Lipophilic Balance) in the range of 4 to 10 are preferred. In addition, the acyl group constituting the hydrophobic group may be any of the saturated, unsaturated, straight or branched acyl groups, and it is preferred that the acyl group have 12 to 18 carbon atoms. Examples of such sorbitan fatty acid esters include sorbitan monolaurate, sorbitan monopalmitate and sorbitan monoleate, and these may be suitably used in the aforementioned coating material. It is noted here that the aforementioned sugar alcohol derivative-type surfactant may be used in combination as long as the amount thereof is within the range which does not impair the gas barrier properties.

When the aforementioned coating material comprises the sugar alcohol derivative-type surfactant, the mass ratio of the high hydrogen-bonding resin and the swelling clay is preferably 2:8 to 5:5, more preferably 2:8 to 4:6, still more preferably 2:8 to 3:7. When the mass ratio of the high hydrogen-bonding resin and the swelling clay is not higher than 1:9, the coating material becomes highly viscous, making the coating operation difficult. In this case, coating may become possible by lowering the concentration of the coating material with an addition of a solvent. However, there may arise another problem such as prolonged production time. Further, when the mass ratio of the high hydrogen-bonding resin and the swelling clay becomes not less than 6:4, gas barrier properties equivalent or superior to those of a packaging material such as PTP sheet may not be attained.

Although the content of the aforementioned sugar alcohol derivative-type surfactant varies depending on the ratio of the aforementioned high hydrogen-bonding resin and the aforementioned swelling clay, it is preferably 7 to 35%, more preferably 10 to 30%, still more preferably 12 to 24%. The term "the content of the sugar alcohol derivative-type surfactant" refers to a ratio (%) of the sugar alcohol derivative-type surfactant with respect to the entire mixture obtained by adding the sugar alcohol derivative-type surfactant to the high hydrogen-bonding resin and the swelling clay. By adding such sugar alcohol derivative-type surfactant, coating of the solid formulation becomes easy and the gas barrier properties of the resulting coating film are improved. However, depending on the mass ratio of the high hydrogen-bonding resin and the swelling clay, when the content of the sugar alcohol derivative-type surfactant becomes not higher than 6% or not less than 36%, gas barrier properties equivalent or superior to those of a packaging material such as PTP sheet may not be attained.

In the aforementioned coating material, a pharmacologically acceptable additive may be added as long as the amount thereof is within the range which does not impair the gas barrier properties. For example, by adding a sugar or sugar alcohol such as maltose, maltitol, sorbitol, xylitol, fructose, glucose, lactitol, isomaltose, lactose, erythritol, mannitol, trehalose or sucrose, croscarmellose sodium or low-substituted hydroxypropyl cellulose as a swelling property-disintegrating agent, the disintegration property of the coating film can be improved, and by adding triethyl citrate, polyethylene glycol or glycerin as a plasticizer, the strength of the coating film can be improved.

Also, an additive which is conventionally used in film-coating by those skilled in the art may be further added to the aforementioned coating material. Examples of such additive include coloring agents such as plant-extract dyes and masking agents such as titanium oxide, calcium carbonate and silicon dioxide.

The solid formulation is characterized by being coated with the aforementioned coating material.

Examples of the aforementioned solid formulation include tablets (including sublingual tablets and orally-disintegrating tablets), capsules (including soft capsules and microcapsules), granules, subtle granules, powders, balls, troches and films.

The aforementioned solid formulation may be one which has a coating film of the aforementioned coating material on the surface thereof having another coating film made of a gastric-soluble or enteric-soluble macromolecular substance or the like, or one which has another coating film made of a gastric-soluble or enteric-soluble macromolecular substance or the like on the surface thereof having a coating film of the aforementioned coating material.

EXAMPLES

The coating and material will now be concretely described by way of examples thereof. However, the disclosure is not restricted thereto.

The dispersion condition of the swelling clay, oxygen permeability coefficient and water vapor permeability were measured by using a coating film (film) obtained from the coating material.

Method of Evaluating the Dispersion Condition of the Swelling Clay

In accordance with a focused ion beam method, the coating film was made thin by a gadolinium ion beam (FB-2000A; Hitachi High-Tech Manufacturing & Service Corporation). The thus obtained thin coating film was observed under a transmission electron microscope (H-9000UHR; Hitachi High-Tech Manufacturing & Service Corporation) to visually measure the number of laminated layers of the swelling clay.

When the swelling clay is oriented planarly to the transverse section of the coating film (cross-section parallel to the coating film surface), a focused and clear micrograph is obtained, so that a single layer of the swelling clay (thickness of about 1 nm) and a laminated structure thereof can be observed. On the other hand, when the swelling clay is not oriented planarly, an unfocused and fuzzy micrograph is obtained. Therefore, the ratio of the laminated structure of the swelling clay oriented planarly to the transverse section of the coating film was calculated by dividing the area of the focused micrograph of the laminated structure by the area of the observation region (2.5 μm×2.5 μm square). The area was expressed in a numerical value by performing image analysis with NIHimage.

Method of Measuring the Oxygen Permeability Coefficient

In accordance with a standard specification in the art, JIS K7126-1 (2006) (Gas Permeability Test Method by Gas Chromatography), the oxygen permeability coefficient was measured at a temperature of 23±2° C. in relative humidities of 0% (0% RH) and 90% (90% RH) by using an oxygen permeability coefficient measuring apparatus (GTR-30XAD2 and G2700T·F; GTR Tec Corporation). Hereinafter, relative humidity is abbreviated as "RH." Method of measuring the water vapor permeability A standard specification in the art, JIS K8123 (1994), was partially modified to measure the water vapor permeability. First, a coating film prepared by the method described below was held up to the light and a circular piece having a diameter of 3.5 cm was excised from a portion of the coating film having no pinhole and uniform thickness. The thickness of the coating film was measured at 5 arbitrary spots. Next, 3 g of calcium chloride (particle size of 850 to 2,000 μm) was placed in an aluminum cup (diameter of 30 mm), and the thus excised circular coating film and a film-fixing ring were placed in the order mentioned onto the aluminum cup. The ring was fixed by placing a weight thereon. In this condition, molten paraffin wax was poured into the margin of the aluminum cup. After the paraffin wax was solidified, the weight was removed and the mass of the entire aluminum cup was measured as the initial mass. Then, the aluminum cup was placed in a thermostat bath at 40° C. and 75% RH. The aluminum cup was removed every 24 hours to measure the mass thereof, and the water vapor permeability was calculated using the following equation. It should be noted here that, in all of the below-described tests for measuring the water vapor permeability, the following applied: r=1.5 cm, t=24 hours and C=1 atm.

Water vapor permeability P (g·mm/cm$^2$·24 hr·atm)=W·A/B·t·C

W: Increased mass in 24 hours (g)
A: Average thickness of the coating film at 5 spots (mm)
B: Permeation area πr$^2$ (cm$^2$)
t: Elapsed time (hr)
C: Atmospheric pressure (atm)

Reference Example 1

Preparation of a Polyvinyl Alcohol-Based Coating Film

To 42.5 parts by mass of water, 7.5 parts by mass of OPADRY II HP (registered trademark) (Colorcon Japan) was added, and the resulting mixture was stirred to obtain a dispersion. Then, the thus obtained dispersion was poured into a polypropylene tray having a flat bottom and dried overnight in a 50° C. oven in a leveled condition to obtain a coating film. This coating film was a polyvinyl alcohol (PVA)-based coating film. Hereinafter, polyvinyl alcohol is abbreviated as "PVA."

Reference Example 2

Preparation of a Modified PVA-Based Coating Film

To 45.0 parts by mass of water, 3.5 parts by mass of POVA-COAT (registered trademark) (Nisshin Kasei Co., Ltd.), 1.0 parts by mass of titanium oxide and 0.5 parts by mass of talc were added, and the resulting mixture was stirred to obtain a dispersion. A coating film was then obtained in the same manner as in Reference Example 1. This coating film was a modified PVA-based coating film.

Reference Example 3

Preparation of a Sodium Carboxymethyl Cellulose-Based Coating Film

To 46.5 parts by mass of water, 3.5 parts by mass of OPA-GLOS2 (registered trademark) (Colorcon Japan) was added, and the resulting mixture was stirred to obtain a dispersion. A coating film was obtained in the same manner as in Reference Example 1. This coating film was a sodium carboxymethyl cellulose (CMC)-based coating film. Hereinafter, sodium carboxymethyl cellulose is abbreviated as "CMC."

Table 1 shows the results of the measurements of the oxygen permeability coefficient and the water vapor permeability of the coating films of Reference Examples 1 to 3 used for coating solid formulations.

exchange capacity: 115 meq/100 g) to 968 parts by mass of stirred water; uniformly dispersing the resulting mixture using a homogenizer; and then suction-filtrating the resultant through a filter paper. Hereinafter, bentonite is abbreviated as "BT."

The thus obtained dispersion was sprayed onto the back side of the polypropylene balance tray and immediately dried with hot air using a dryer. After repeating several rounds of the spraying and dryer drying, the balance tray was altogether placed in a 50° C. oven and dried overnight. Subsequently, a coating film was separated from the balance tray to obtain the coating film of Example 1.

Example 2

To 137.0 parts by mass of water, 2.64 parts by mass of PVA (EG-05; Nippon Synthetic Chemical Industry Co., Ltd.), 192.5 parts by mass of 3.2% BT solution and 1.2 parts by mass of sorbitan monolaurate (Span20; Wako Pure Chemical Industries, Ltd.) were added, and the resulting mixture was stirred using the homogenizer (Polytron Model KR) to obtain a dispersion. From this dispersion, the coating film of Example 2 was obtained in accordance with the method of Example 1.

Comparative Example 1

To 42.55 parts by mass of water, 1.2 parts by mass of hydroxypropylmethyl cellulose (TC-5W; Shin-Etsu Chemical Co., Ltd.) and 56.25 parts by mass of 3.2% BT solution were added, and the resulting mixture was stirred using the homogenizer (Polytron Model KR) to obtain a dispersion. From this dispersion, the coating film of Comparative Example 1 was obtained in accordance with the method of Example 1. Hereinafter, hydroxypropylmethyl cellulose is abbreviated as "HPMC."

TABLE 1

|  |  | PTP packaging material (moisture-resistant PTP) | Reference Example 1 (PVA-based coating film) | Reference Example 2 (modified PVA-based coating film) | Reference Example 3 (CMC-based coating film) |
|---|---|---|---|---|---|
| Oxygen permeability coefficient ($cm^3 \cdot mm/cm^2 \cdot 24\ hr \cdot atm$) | 23° C., 0% RH | No Data | $1.5 \times 10^{-2}$ | No Data | $3.0 \times 10^{-6}$ |
|  | 23° C., 90% RH | $4.0 \times 10^{-5}$ | $4.4 \times 10$ | $3.6 \times 10^{-4}$ | $2.6 \times 10^{-4}$ |
| Water vapor permeability ($g \cdot mm/cm^2 \cdot 24\ hr \cdot atm$) | 40° C., 75% RH | $3.3 \times 10^{-5}$ | $3.1 \times 10^{-3}$ | $6.1 \times 10^{-4}$ | $5.3 \times 10^{-3}$ |

From Table 1, it became apparent that only the PTP packaging material had both the oxygen permeability coefficient and the water vapor permeability at less than $1 \times 10^{-4}$ and that the gas barrier properties of the coating films of Reference Examples 1 to 3 used for coating solid formulations were markedly inferior compared to those of the PTP packaging material.

Example 1

To 42.55 parts by mass of water, 1.2 parts by mass of PVA (EG-05; Nippon Synthetic Chemical Industry Co., Ltd.) and 56.25 parts by mass of 3.2% bentonite solution were added, and the resulting mixture was stirred using a homogenizer (Polytron Model KR) to obtain a dispersion. The 3.2% bentonite solution was prepared by adding 32 parts by mass of bentonite (Kunipia-F; Kunimine Industries Co., Ltd.) (cation Comparative Example 2

To 96.4 parts by mass of water, 10.0 parts by mass of PVA was added, and the resulting mixture was stirred using a stirrer to obtain a dispersion. From this dispersion, the coating film of Comparative Example 2 was obtained in accordance with the method of Example 1.

Comparative Example 3

To 56.7 parts by mass of water, 2.64 parts by mass of PVA, 6.16 parts by mass of talc and 1.2 parts by mass of sorbitan monolaurate were added, and the resulting mixture was stirred using the homogenizer to obtain a dispersion. From this dispersion, the coating film of Comparative Example 3 was obtained in accordance with the method of Example 1.

Table 2 shows the results of the measurements of the oxygen permeability coefficient and the water vapor permeability of the coating films obtained in Examples 1 and 2 and Comparative Examples 1 to 3.

TABLE 2

|  |  | Example 1 | Example 2 | Comparative Example 1 | Comparative Example 2 | Comparative Example 3 |
|---|---|---|---|---|---|---|
| PVA or HPMC/BT or talc/sorbitan monolaurate (mass ratio) |  | 4/6/0 | 26.4/61.6/12 | 4/6/0 | 10/0/0 | 26.4/61.6/12 |
| Oxygen permeability coefficient ($cm^3 \cdot mm/cm^2 \cdot 24\ hr \cdot atm$) | 23° C., 90% RH | $7.0 \times 10^{-6}$ | $3.2 \times 10^{-6}$ | No Data | $5.7 \times 10^{-5}$ | No Data |
| Water vapor permeability coefficient ($g \cdot mm/cm^2 \cdot 24\ hr \cdot atm$) | 40° C., 75% RH | $3.4 \times 10^{-5}$ | $1.9 \times 10^{-5}$ | $3.9 \times 10^{-4}$ | $9.1 \times 10^{-4}$ | $1.1 \times 10^{-3}$ |

As a result, it was revealed that, compared to HPMC, PVA, that is, a high hydrogen-bonding resin, exhibited more prominent effect to decrease the oxygen permeability coefficient and the water vapor permeability of the coating film (comparison between Example 1 and Comparative Example 1). In addition, when BT, that is, a swelling clay, was contained in the coating film, the oxygen permeability coefficient and the water vapor permeability of the coating film were both markedly decreased (comparison between Example 1 and Comparative Example 2), and this effect was more prominent compared to the case in which talc was used in place of BT (comparison between Example 2 and Comparative Example 3). From these results, it was revealed that the coating film of Example 1 comprising PVA and BT at a particular ratio and the coating film of Example 2 comprising PVA, BT and sorbitan monolaurate at a particular ratio had both the oxygen permeability coefficient and the water vapor permeability at less than $1 \times 10^{-4}$ and that, therefore, these coating films had gas barrier properties equivalent or superior to those of the PTP packaging material.

Measurement of the Coating Films Under a Transmission Electron Microscope

Figure 2:
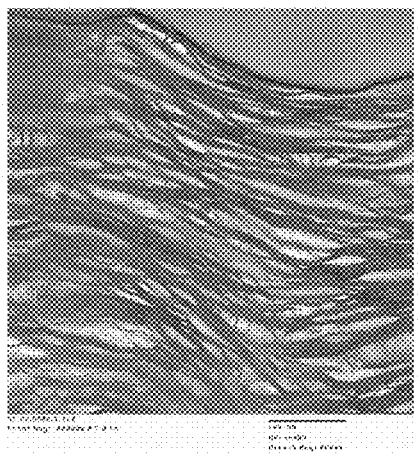
FIG. 2 shows a focused ion beam-transmission electron micrograph of the coating film of Example 2.

Using a focused ion beam method, the longitudinal section of the coating films of Examples 1 and 2 were observed under a transmission electron microscope. FIGS. 1 and 2 show micrographs of Examples 1 and 2, respectively. the coating film of Example 3 was obtained in accordance with the method of Example 1. Using a focused ion beam method, the longitudinal section of the coating film of Example 3 was observed under a transmission electron microscope. The micrograph thereof is shown in FIG. 3.

Comparative Example 4

To 33.5 parts by mass of water, 0.9 parts by mass of PVA and 65.6 parts by mass of 3.2% BT solution were added, and the coating film of Comparative Example 4 was obtained in accordance with the method of Example 1. The cross section of the coating film was observed in accordance with the method of Example 3. The micrograph thereof is shown in FIG. 4.

Comparative Example 5

Figure 5:
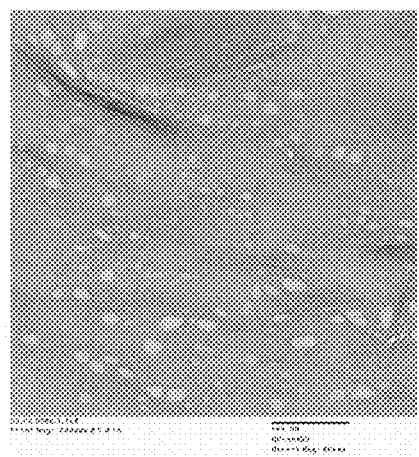
FIG. 5 shows a focused ion beam-transmission electron micrograph of the coating film of Comparative Example 5.

To 89.9 parts by mass of water, 2.25 parts by mass of PVA and 7.8 parts by mass of 3.2% BT solution were added, and the coating film of Comparative Example 5 was obtained in accordance with the method of Example 1. The cross section of the coating film was observed in accordance with the method of Example 3. The micrograph thereof is shown in FIG. 5.

Table 3 shows the dispersion condition of BT, as well as the oxygen permeability coefficient and the water vapor permeability of the coating films obtained in Examples 1 to 3 and Comparative Examples 4 and 5.

Example 3

To 51.6 parts by mass of water, 1.5 parts by mass of PVA and 46.9 parts by mass of 3.2% BT solution were added, and

TABLE 3

|  | Example 1 | Example 2 | Example 3 | Comparative Example 4 | Comparative Example 5 |
|---|---|---|---|---|---|
| PVA/BT/sorbitan monolaurate | 4/6/0 | 26.4/61.6/12 | 5/5/0 | 3/7/0 | 9/1/0 |
| Ratio of the planarly-oriented BT laminated structures (%) | 51 | 42 | 53 | 20 | 4 |
| Network structures of BT | present | present | present | present | not present |
| Oxygen permeability coefficient ($cm^3 \cdot mm/cm^2 \cdot 24\ hr \cdot atm$) | $7.0 \times 10^{-6}$ | $3.2 \times 10^{-6}$ | $2.6 \times 10^{-5}$ | $8.3 \times 10^{-3}$ | No Data |
| Water vapor permeability ($g \cdot mm/cm^2 \cdot 24\ hr \cdot atm$) | $3.4 \times 10^{-5}$ | $1.9 \times 10^{-5}$ | $2.5 \times 10^{-5}$ | $5.2 \times 10^{-5}$ | $2.3 \times 10^{-4}$ |

As a result, it was revealed that gas barrier properties equivalent or superior to those of the PTP packaging material can be attained when the ratio of the BT laminated structures oriented planarly to the transverse section of the coating film is not less than 30%.

Example 4

Following the constitution shown in Table 4, water, PVA and BT solution were mixed, and a coating film was obtained in accordance with the method of Example 1. The oxygen permeability coefficient (23° C., 90% RH) and the water vapor permeability (40° C., 75% RH) were measured.

Comparative Example 6

Following the constitution shown in Table 4, water, PVA and BT solution were mixed, and a dispersion was obtained in accordance with the method of Example 1. A coating film was then obtained by the method of Example 1, and the oxygen permeability coefficient (23° C., 90% RH) and the water vapor permeability (40° C., 75% RH) were measured.

Table 4 shows the effects of the mass ratio of PVA and BT (PVA/BT) on the oxygen permeability coefficient and the water vapor permeability.

TABLE 4

|  | PVA/BT | Oxygen permeability coefficient ($cm^3 \cdot mm/cm^2 \cdot 24\,hr \cdot atm$) | Water vapor permeability ($g \cdot mm/cm^2 \cdot 24\,hr \cdot atm$) |
| --- | --- | --- | --- |
| Example 1 | 4/6 | $7.0 \times 10^{-6}$ | $3.4 \times 10^{-5}$ |
| Example 3 | 5/5 | $2.6 \times 10^{-5}$ | $2.5 \times 10^{-5}$ |
| Example 4 | 6/4 | $1.6 \times 10^{-5}$ | $3.2 \times 10^{-5}$ |
| Comparative Example 4 | 3/7 | $8.3 \times 10^{-3}$ | $5.2 \times 10^{-5}$ |
| Comparative Example 6 | 7/3 | No Data | $1.6 \times 10^{-4}$ |

As a result, it was revealed that, when the mass ratio of PVA and BT (PVA/BT) is 4:6 to 6:4 (4/6 to 6/4), the oxygen permeability coefficient and the water vapor permeability both becomes less than $1 \times 10^{-4}$ and that, therefore, gas barrier properties equivalent or superior to those of the PTP packaging material can be attained.

Examples 5 to 7 and Comparative Examples 7 to 9

Water, PVA, BT solution and respective surfactant were mixed and a dispersion was obtained in accordance with the method of Example 2. A coating film was then obtained by the method of Example 1, and the oxygen permeability coefficient (23° C., 90% RH) and the water vapor permeability (40° C., 75% RH) were measured.

Table 5 shows the effects of the type of the surfactant on the oxygen permeability coefficient and the water vapor permeability. The evaluations were carried out by fixing the mass ratio of PVA, BT and the respective surfactant at 26.4:61.6:12 (26.4/61.6/12).

TABLE 5

|  | Surfactant | Oxygen permeability coefficient ($cm^3 \cdot mm/cm^2 \cdot 24\,hr \cdot atm$) | Water vapor permeability ($g \cdot mm/cm^2 \cdot 24\,hr \cdot atm$) |
| --- | --- | --- | --- |
| Example 2 | Sorbitan monolaurate | $3.2 \times 10^{-6}$ | $1.9 \times 10^{-5}$ |
| Example 5 | Sorbitan monopalmitate | $1.6 \times 10^{-5}$ | $6.0 \times 10^{-5}$ |
| Example 6 | Sorbitan monooleate | $2.2 \times 10^{-5}$ | $2.9 \times 10^{-5}$ |
| Example 7 | Sucrose stearate | $1.4 \times 10^{-5}$ | $1.9 \times 10^{-5}$ |
| Comparative Example 7 | No surfactant | $8.3 \times 10^{-3}$ | $5.2 \times 10^{-5}$ |
| Comparative Example 8 | Pluronic | $7.3 \times 10^{-4}$ | $1.9 \times 10^{-5}$ |
| Comparative Example 9 | Polyoxyethylene hydrogenated castor oil | $4.4 \times 10^{-2}$ | $4.7 \times 10^{-5}$ |

As a result, it was revealed that, in addition to the addition of sorbitan monolaurate, the addition of sorbitan monopalmitate, sorbitan monooleate or sucrose stearate makes both of the oxygen permeability coefficient and the water vapor permeability to become less than $1 \times 10^{-4}$ and that, therefore, gas barrier properties equivalent or superior to those of the PTP packaging material can be attained. This suggests that the sugar alcohol derivative-type surfactants contribute to an improvement of gas barrier properties.

Examples 8 to 10

Following the constitution shown in Table 6, water, PVA, BT solution and sorbitan monolaurate were mixed, and a dispersion was obtained in accordance with the method of Example 1. A coating film was then obtained by the method of Example 1, and the oxygen permeability coefficient (23° C., 90% RH) and the water vapor permeability (40° C., 75% RH) were measured.

Comparative Examples 10 and 11

Following the constitution shown in Table 6, water, PVA, BT solution and sorbitan monolaurate were mixed, and a dispersion was obtained in accordance with the method of Example 2. A coating film was then obtained by the method of Example 1, and the oxygen permeability coefficient (23° C., 90% RH) and the water vapor permeability (40° C., 75% RH) were measured.

Table 6 shows the effects of the mass ratio of PVA and BT (PVA/BT) on the oxygen permeability coefficient and the water vapor permeability. The content of sorbitan monolaurate was set at 12% in all of the cases.

TABLE 6

|  | PVA/BT/sorbitan monolaurate | PVA/BT | Oxygen permeability coefficient ($cm^3 \cdot mm/cm^2 \cdot 24\,hr \cdot atm$) | Water vapor permeability ($g \cdot mm/cm^2 \cdot 24\,hr \cdot atm$) |
| --- | --- | --- | --- | --- |
| Example 8 | 17.6/70.4/12 | 2/8 | $3.8 \times 10^{-5}$ | $5.0 \times 10^{-5}$ |
| Example 9 | 35.2/52.8/12 | 4/6 | $3.9 \times 10^{-5}$ | $5.7 \times 10^{-5}$ |
| Example 10 | 44/44/12 | 5/5 | $5.4 \times 10^{-5}$ | $2.5 \times 10^{-5}$ |
| Comparative Example 10 | 52.8/35.2/12 | 6/4 | $1.1 \times 10^{-2}$ | $4.2 \times 10^{-5}$ |
| Comparative Example 11 | 52.8/35.2/12 | 1/9 | $1.9 \times 10^{-5}$ | $1.9 \times 10^{-4}$ |

As a result, it was revealed that, when the mass ratio of PVA and BT (PVA/BT) is 2:8 to 5:5 (2/8 to 5/5), the addition of sorbitan monolaurate makes both of the oxygen permeability coefficient and the water vapor permeability to become less than $1 \times 10^{-4}$ and that, therefore, gas barrier properties equivalent or superior to those of the PTP packaging material can be attained.

Examples 11 and 12 and Comparative Example 12

Following the constitution shown in Table 7, water, PVA, BT solution and sorbitan monolaurate were mixed, and a dispersion was obtained in accordance with the method of Example 2. A coating film was then obtained by the method of Example 1, and the oxygen permeability coefficient (23° C., 90% RH) and the water vapor permeability (40° C., 75% RH) were measured.

Table 7 shows the effects of the sorbitan monolaurate content on the oxygen permeability coefficient and the water vapor permeability. The evaluations were carried out by fixing the mass ratio of PVA and BT (PVA/BT) at 5:5 (5/5).

TABLE 7

| | PVA/BT/ sorbitan monolaurate | PVA/ BT | Oxygen permeability coefficient ($cm^3 \cdot mm/ cm^2 \cdot 24\ hr \cdot atm$) | Water vapor permeability ($g \cdot mm/ cm^2 \cdot 24\ hr \cdot atm$) |
|---|---|---|---|---|
| Example 3 | 50/50/0 | 5/5 | $2.6 \times 10^{-5}$ | $2.5 \times 10^{-5}$ |
| Example 10 | 44/44/12 | 5/5 | $5.4 \times 10^{-5}$ | $3.4 \times 10^{-5}$ |
| Example 11 | 47/47/6 | 5/5 | $1.4 \times 10^{-5}$ | $3.1 \times 10^{-5}$ |
| Example 12 | 38/38/24 | 5/5 | $5.3 \times 10^{-5}$ | $5.6 \times 10^{-5}$ |
| Comparative Example 12 | 32/32/36 | 5/5 | $8.7 \times 10^{-5}$ | $1.2 \times 10^{-4}$ |

As a result, it was revealed that, when PVA/BT=5/5, the sorbitan monolaurate content in the range of 0 to 24% makes both of the oxygen permeability coefficient and the water vapor permeability to be less than $1 \times 10^{-4}$ and that, therefore, gas barrier properties equivalent or superior to those of the PTP packaging material can be attained.

Examples 13 and 14 and Comparative Examples 13 and 14

Following the constitution shown in Table 8, water, PVA, BT solution and sorbitan monolaurate were mixed, and a dispersion was obtained in accordance with the method of Example 2. A coating film was then obtained by the method of Example 1, and the oxygen permeability coefficient (23° C., 90% RH) and the water vapor permeability (40° C., 75% RH) were measured.

Table 8 shows the effects of the sorbitan monolaurate content on the oxygen permeability coefficient and the water vapor permeability. The evaluations were carried out by fixing the mass ratio of PVA and BT (PVA/BT) at 2:8 (2/8).

TABLE 8

| | PVA/BT/ sorbitan monolaurate | PVA/ BT | Oxygen permeability coefficient ($cm^3 \cdot mm/ cm^2 \cdot 24\ hr \cdot atm$) | Water vapor permeability ($g \cdot mm/ cm^2 \cdot 24\ hr \cdot atm$) |
|---|---|---|---|---|
| Example 8 | 17.6/70.4/12 | 2/8 | $3.8 \times 10^{-5}$ | $5.0 \times 10^{-5}$ |
| Example 13 | 15.2/60.8/24 | 2/8 | No Data | $6.9 \times 10^{-5}$ |
| Example 14 | 12.8/51.2/36 | 2/8 | $8.1 \times 10^{-5}$ | $7.9 \times 10^{-5}$ |
| Comparative Example 13 | 18.8/75.2/6 | 2/8 | $2.7 \times 10^{-3}$ | $5.0 \times 10^{-5}$ |
| Comparative Example 14 | 10.4/41.6/48 | 2/8 | No Data | $1.0 \times 10^{-4}$ |

As a result, it was revealed that, when PVA/BT=2/8, the sorbitan monolaurate content in the range of 12 to 36% makes both of the oxygen permeability coefficient and the water vapor permeability to be less than $1 \times 10^{-4}$ and that, therefore, gas barrier properties equivalent or superior to those of the PTP packaging material can be attained.

Comparative Example 15

Production of an Ascorbic Acid-Containing Tablet

To evaluate the barrier properties against oxygen and water vapor, an ascorbic acid-containing tablet which is unstable against oxygen and water vapor was produced.

First, lactose, crystalline cellulose and hydroxypropyl cellulose-SL were loaded into a vertical granulator and granulated with water in which cupric sulfate pentahydrate had been dissolved. The thus obtained granules were dried overnight at 50° C. and pulverized using a comil to obtain granules A. Then, the granules A and ascorbic acid were loaded into a vertical granulator and after granulation with ethanol, the resultant was dried at 50° C. for 2 hours and pulverized using a comil to obtain granules B. Subsequently, the granules B, a low-substituted hydroxypropyl cellulose, croscarmellose sodium and magnesium stearate were mixed, and the resultant was tableted using a rotary tableting machine (Kikusui Chemical Industries Co., Ltd.) to obtain an ascorbic acid-containing tablet (diameter of 8 mm, 12R). The thus obtained ascorbic acid-containing tablet not coated with a coating material was used as Comparative Example 15.

Example 15

Production of an Ascorbic Acid-Containing Coated Tablet Coated with the Dispersion of Example 2

To a coating pan (Hi-Coater mini; Freund Corporation), 400 g of the ascorbic acid tablet of Comparative Example 15 was loaded, and the dispersion prepared in Example 2 was used as the coating material to coat the ascorbic acid-containing tablet. The coating with the coating material was performed to a coating thickness of 60 μm to obtain an ascorbic acid-containing coated tablet. The thus obtained ascorbic acid-containing coated tablet coated with the dispersion of Example 2 was used as Example 15.

Comparative Example 16

Production of an Ascorbic Acid-Containing Coated Tablet Coated with the Dispersion of Reference Example 3

To the coating pan (Hi-Coater mini; Freund Corporation), 400 g of the ascorbic acid tablet of Comparative Example 15 was loaded, and the dispersion prepared in Reference Example 3 was used as the coating material to coat the tablet. The coating with the coating material was performed to a coating thickness of 60 μm. The thus obtained ascorbic acid-containing coated tablet coated with the dispersion of Reference Example 3 was used as Comparative Example 16.

The Disintegration Property of the Ascorbic Acid-Containing Coated Tablet

The disintegration property of the ascorbic acid-containing coated tablet of Example 15 was evaluated using an elution tester. That is, one ascorbic acid-containing coated tablet was placed in 900 mL of water which had been heated to 37° C., and the time required for the coating film to start to detach from the tablet surface was measured. As the result, the time required for the coating film to start to detach from the tablet surface was about 2 minutes. Consequently, it was revealed that the ascorbic acid-containing coated tablet of Example 15 has excellent disintegration property, and it was suggested that the dispersion of Example 2 may be applied in coating not only sustained release formulations, but also immediate release formulations.

The storage stability of the ascorbic acid-containing coated tablets

The ascorbic acid-containing tablet of Comparative Example 15 and the ascorbic acid-containing coated tablets of Example 15 and Comparative Example 16 were stored for 4 weeks in an open condition or an airtight condition in a desiccator at 25° C. and 95% RH to evaluate the residual ratio of ascorbic acid (drug residual ratio) with time. The term "in an open condition" means to place each tablet as is in the desiccator, and the term "in an airtight condition" means to put each tablet into a glass bottle having a plastic inner lid and outer lid, which bottle is then sealed, and place the glass bottle in the desiccator while maintaining the sealed condition.

Figure 6:
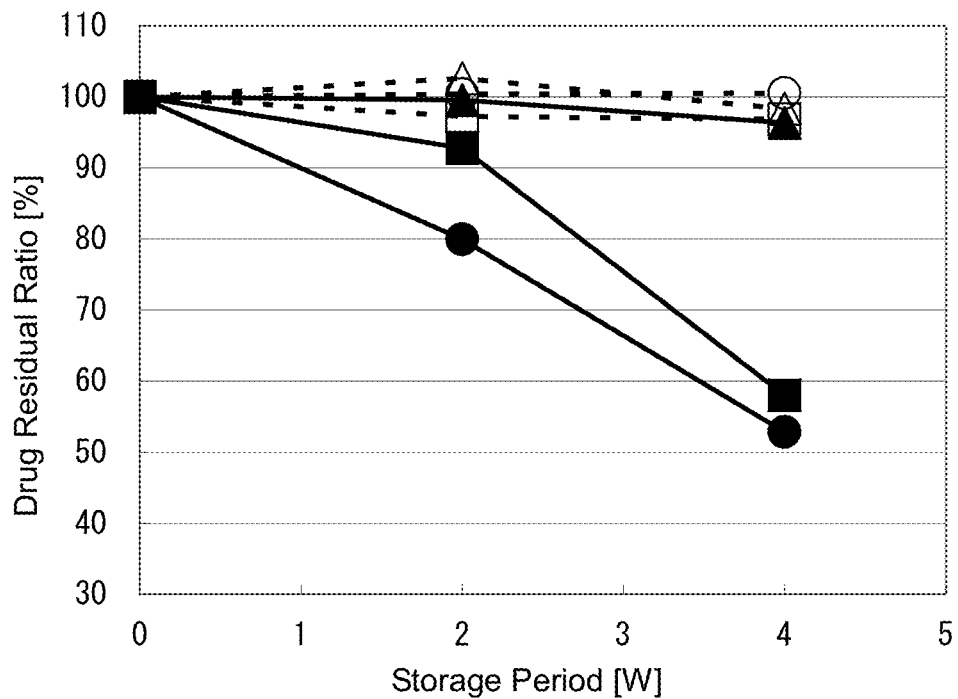
FIG. 6 is a graph showing the changes with time in the drug residual ratio of the ascorbic acid tablet.

FIG. 6 is a graph showing the changes with time in the drug residual ratio. In FIG. 6, the open triangle (△), filled triangle (▲), open square (□), filled square (■), open circle (○) and filled circle (●) represent the results of: the ascorbic acid-containing coated tablet of Example 15 placed in an airtight condition; the ascorbic acid-containing coated tablet of Example 15 in an open condition; the ascorbic acid-containing coated tablet of Comparative Example 16 placed in an airtight condition; the ascorbic acid-containing coated tablet of Comparative Example 16 placed in an open condition; the ascorbic acid-containing tablet of Comparative Example 15 placed in an airtight condition; and the ascorbic acid-containing tablet of Comparative Example 15 placed in an open condition, respectively. In addition, the ordinate and the abscissa indicate the drug residual ratio (%) and the storage period (W), respectively, and the W means weeks.

In the ascorbic acid-containing tablet of Comparative Example 15 and the ascorbic acid-containing coated tablet of Comparative Example 16 in an open condition, the drug residual ratio decreased with time. However, in the ascorbic acid-containing coated tablet of Example 15 in an open condition, degradation of the drug was not observed even after the 4-week storage and the stability was maintained at a level equivalent to the case where the tablet was placed in an airtight condition. Accordingly, it was revealed that the ascorbic acid-containing coated tablet of Example 15 has high barrier properties against oxygen and water vapor.

Comparative Example 17

Production of a Propantheline Bromide-Containing Tablet

To evaluate gas barrier properties, a propantheline bromide-containing tablet known to be extremely unstable in unpacked condition was produced. A propantheline bromide-containing tablet (Methaphyllin (registered trademark); Eisai Co., Ltd.) was pulverized using a mortar in a dry box to prevent moisture absorption, and the thus obtained granules of the pulverized tablet were again tableted using a rotary tableting machine (Kikusui Chemical Industries Co., Ltd.) to obtain a propantheline bromide-containing tablet (diameter of 8 mm, 12R). The thus obtained propantheline bromide-containing tablet not coated with a coating material was used as Comparative Example 17.

Example 16

Production of a Propantheline Bromide-Containing Coated Tablet Coated with the Dispersion of Example 2

To the coating pan (Hi-Coater mini; Freund Corporation), 400 g of the propantheline bromide-containing tablet of Comparative Example 17 was loaded, and the dispersion prepared in Example 2 was used as the coating material to coat the propantheline bromide-containing tablet. The coating with the coating material was performed to a coating thickness of 60 μm to obtain a propantheline bromide-containing coated tablet. The thus obtained propantheline bromide-containing coated tablet was used as Example 16.

Comparative Example 18

Production of a Propantheline Bromide-Containing Coated Tablet Coated with a Commercially-Available General-Purpose Coating Formulation Solution To distilled water, a mixture of hydroxypropylmethyl cellulose 2910, titanium oxide and Macrogol 400 (Opadry OY-7300(registered trademark); Colorcon Japan) was added and dissolved to obtain a commercially-available general-purpose coating formulation solution. To the coating pan (Hi-Coater mini; Freund Corporation), 400 g of the propantheline bromide-containing tablet of Comparative Example 17 was loaded, and the commercially-available general-purpose coating formulation solution was used as the coating material to coat the tablet. The coating with the coating material was performed to a coating thickness of 60 μm. The thus obtained propantheline bromide-containing coated tablet was used as Comparative Example 18.

Comparative Example 19

Production of a Propantheline Bromide-Containing Coated Tablet Coated with a Commercially-Available Moisture-Resistant Formulation Solution Sodium lauryl sulfate (15 g) was added to distilled water (875 g) and the resultant was stirred until the sodium lauryl sulfate was completely dissolved. Next, aminoalkyl methacrylate copolymer E (Eudragit EPO (registered trademark); Degusssa Co.) (100 g) was added and stirred, and when it was uniformly dispersed, stearic acid (10 g) was added. The resultant was further stirred to obtain a commercially-available moisture-resistant formulation solution. To the coating pan (Hi-Coater mini; Freund Corporation), 400 g of the propantheline bromide-containing tablet of Comparative Example 17 was loaded, and the commercially-available moisture-resistant coating formulation solution was used as the coating material to coat the tablet. The coating with the coating material was performed to a coating thickness of 60 μm. The thus obtained propantheline bromide-containing coated tablet was used as Comparative Example 19.

Comparative Example 20

Propantheline Bromide Sugar-Coated Tablet

A propantheline bromide tablet (Pro-Banthine (registered trademark); Pfizer Inc.) as is, was used as the propantheline bromide sugar-coated tablet of Comparative Example 20.

The Storage Stability of the Propantheline Bromide-Containing Coated Tablets and the Propantheline Bromide Sugar-Coated Tablet The propantheline bromide-containing tablet of Comparative Example 17, the propantheline bromide-containing coated tablets of Example 16 and Comparative Examples 18 and 19, and the propantheline bromide sugar-coated tablet of Comparative Example 20 were each stored for 2 months in an open condition in a desiccator at 30° C. and 75% RH to evaluate the residual ratio of propantheline bromide (drug residual ratio) with time. The term "in an open condition" means to put each tablet in a glass bottle and place the glass bottle as is without any covering in the desiccator.

Figure 7:
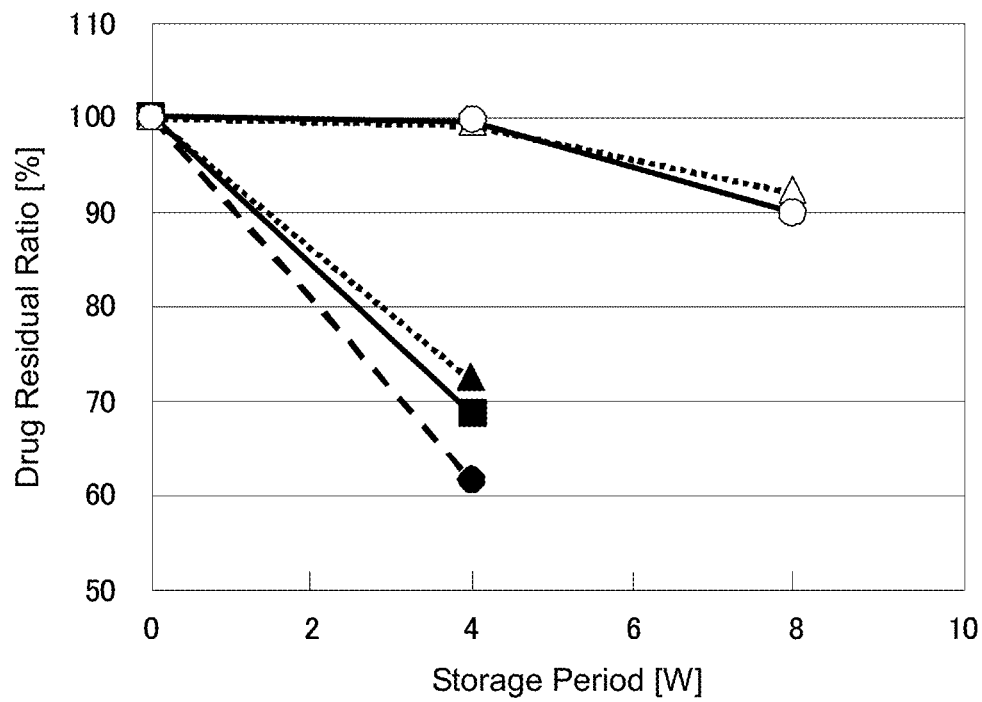
FIG. 7 is a graph showing the changes with time in the drug residual ratio of the propantheline bromide tablet.

FIG. 7 is a graph showing the changes with time in the residual ratio of propantheline bromide (drug residual ratio). In FIG. 7, the open circle (○), filled circle (●), filled square (■), filled triangle (▲) and open triangle (Δ) represent the results of: the propantheline bromide-containing coated tablet of Example 16; the propantheline bromide-containing tablet of Comparative Example 17; the propantheline bromide-containing coated tablet of Comparative Example 18; the propantheline bromide-containing coated tablet of Comparative Example 19; and the propantheline bromide sugar-coated tablet of Comparative Example 20, respectively. In addition, the ordinate and the abscissa indicate the drug residual ratio (%) and the storage period (W), respectively, and the W means weeks.

As a result, in the propantheline bromide-containing tablet of Comparative Example 17, as well as in the propantheline bromide-containing coated tablets of Comparative Example 18 and Comparative Example 19, the drug residual ratio markedly decreased during the 4-week storage in an open condition. However, in the propantheline bromide-containing coated tablet of Example 16 and the propantheline bromide sugar-coated tablet of Comparative Example 20, degradation of the drug was not observed even after the 4-week storage in an open condition.

In addition, in the propantheline bromide-containing coated tablet of Example 16 and the propantheline bromide sugar-coated tablet of Comparative Example 20, when they were stored in an open condition for 8 weeks, a minor decrease in their drug residual ratio was observed. However, there was no significant difference in their drug residual ratios. Therefore, it was revealed that the propantheline bromide-containing coated tablet of Example 16 has high barrier properties at a level equivalent to the propantheline bromide sugar-coated tablet.

Furthermore, in the propantheline bromide sugar-coated tablet of Comparative Example 20, when it was stored in an open condition for 8 weeks, there was confirmed an adhesion to the wall of the glass bottle and between the propantheline bromide sugar-coated tablets caused by melting of the sugar coat and a deterioration in the quality was observed. However, in the propantheline bromide-containing coated tablets of Example 16, such an adhesion to the wall of the glass bottle and between the propantheline bromide-containing coated tablet was not observed at all. Therefore, it was revealed that the propantheline bromide-containing coated tablet of Example 16, in an open condition at 30° C. and 75% RH, has a superior apparent stability compared to the propantheline bromide sugar-coated tablet of Comparative Example 20.

From the above Examples, it was demonstrated that the gas barrier coating material is useful as a versatile coating material for solid formulations, especially as a coating film of solid formulations which contain a drug unstable against oxygen and/or water vapor.

Industrial Applicability

The coating material is useful as a coating material for solid formulations, especially as a coating film of solid formulations which contain a drug unstable against oxygen and/or water vapor and our methods are useful in coating solid formulations.

What is claimed is:

1. A method of improving stability of drugs in a solid pharmaceutical formulation against oxygen and water vapor comprising coating the solid pharmaceutical formulation with a coating material including a high hydrogen-bonding resin and a swelling clay and a sugar alcohol derivative surfactant, wherein an amount of the swelling clay in the coating material is 38 wt % to 60 wt % and a mass ratio of said polyvinyl alcohol and said swelling clay is 4:6 to 6:4, and wherein said sugar alcohol derivative surfactant is at least one selected from a group consisting of sorbitan monolaurate, sorbitan monopalmitate, sorbitan monooleate and sucrose stearate, and which said coating material forms a coating film in which laminated structures of said swelling clay are oriented planarly and dispersed in a network fashion.

2. The method according to claim 1, wherein a ratio of an area occupied by said planarly-oriented laminated structures is not less than 30% with respect to an area of the longitudinal section of said coating film.

3. A method of improving gas barrier properties of a solid pharmaceutical formulation against oxygen and water vapor comprising coating the solid pharmaceutical formulation with a coating material including polyvinyl alcohol and a swelling clay, and a sugar alcohol derivative surfactant, wherein an amount of the swelling clay in the coating material is 38 wt % to 60 wt % and a mass ratio of said polyvinyl alcohol and said swelling clay is 4:6 to 6:4 and wherein said sugar alcohol derivative surfactant is at least one selected from the group consisting of sorbitan monolaurate, sorbitan monopalmitate, sorbitan monooleate and sucrose stearate, and which said coating material forms a coating film in which laminated structures of said swelling clay are oriented planarly and dispersed in a network fashion.

4. The method according to claim 3, wherein a ratio of an area occupied by said planarly-oriented laminated structures is not less than 30% with respect to an area of the longitudinal section of said coating film.

5. A method of film-coating a solid pharmaceutical formulation comprising applying a coating material including polyvinyl alcohol in a swelling clay and a sugar alcohol derivative surfactant, to the solid pharmaceutical formulation, wherein an amount of the swelling clay in the coating material is 38 wt % to 60 wt % and a mass ratio of said polyvinyl alcohol and said said swelling clay is 4:6 to 6:4, and wherein said sugar alcohol derivative surfactant is at least one selected from the group consisting of sorbitan monolaurate, sorbitan monopalmitate, sorbitan monooleate and sucrose stearate, and which said coating material forms a coating film in which laminated structures of said swelling clay are oriented planarly and dispersed in a network fashion.

6. The method according to claim 5, wherein a ratio of an area occupied by said planarly-oriented laminated structures is not less than 30% with respect to an area of the longitudinal section of said coating film.

7. A method of manufacturing a solid pharmaceutical formulation comprising coating the solid pharmaceutical formulation with a coating material including polyvinyl alcohol and a swelling clay, and a sugar alcohol derivative surfactant wherein an amount of the swelling clay in the coating material is 38 wt % to 60 wt % and a mass ratio of said polyvinyl alcohol and said swelling clay is 4:6 to 6:4, and wherein said sugar alcohol derivative surfactant is at least one selected from the group consisting of sorbitan monolaurate, sorbitan monopalmitate, sorbitan monooleate and sucrose stearate, and which said coating material forms a coating film in which laminated structures of said swelling clay are oriented planarly and dispersed in a network fashion.

8. The method according to claim 7, wherein a ratio of an area occupied by said planarly-oriented laminated structures is not less than 30% with respect to an area of the longitudinal section of said coating film.

* * * * *

UNITED STATES PATENT AND TRADEMARK OFFICE
CERTIFICATE OF CORRECTION

PATENT NO. : 8,900,606 B2  
APPLICATION NO. : 13/796006  
DATED : December 2, 2014  
INVENTOR(S) : Hayashi et al.

Page 1 of 1

It is certified that error appears in the above-identified patent and that said Letters Patent is hereby corrected as shown below:

In the Claims,

In Column 19, Claim 1

At lines 64 and 65, please change "high hydrogen-bonding resin" to --polyvinyl alcohol--.

Signed and Sealed this  
Fifteenth Day of September, 2015

Michelle K. Lee  
*Director of the United States Patent and Trademark Office*